United States Patent [19]

Arrang et al.

[11] Patent Number: 5,034,539

[45] Date of Patent: Jul. 23, 1991

[54] HISTAMINE DERIVATIVE, PROCESS FOR PREPARING IT AND ITS THERAPEUTIC USE

[75] Inventors: Jean-Michel Arrang, Gif Sur Yvette; Monique Garbarg, Paris, both of France; Walter Schunack, Berlin, Fed. Rep. of Germany; Jean-Charles Schwartz, Paris, France; Ralph O. Lipp, Berlin, Fed. Rep. of Germany

[73] Assignees: Institut National de la Sante et de la Recherche Medicale (INSERM); Bioproject, both of Paris, France

[21] Appl. No.: 414,923

[22] Filed: Sep. 29, 1989

Related U.S. Application Data

[63] Continuation-in-part of Ser. No. 217,222, Jul. 11, 1988, abandoned, which is a continuation-in-part of Ser. No. 901,750, Aug. 29, 1986, Pat. No. 4,767,778.

[30] Foreign Application Priority Data

Apr. 22, 1988 [FR] France ................................. 88 05399
Apr. 21, 1989 [EP] European Pat. Off. ........ 89401143.6

[51] Int. Cl.$^5$ ................. C07D 233/64; A61K 31/415
[52] U.S. Cl. ..................................... 548/344; 514/397
[58] Field of Search ......................... 514/397; 548/344

[56] References Cited

U.S. PATENT DOCUMENTS 4,767,778  8/1988  Arrang et al. ..................... 514/397

OTHER PUBLICATIONS

Chemical Abstracts 85(5):28472; Durant et al. (1976).
Arch. Pharm (Weinheim) 313; 709–714 (1980) Gerhard et al.
Frontiers in Histamine Research (1985), pp. 39–46, Ganellin et al.

Primary Examiner—Frederick E. Waddell
Assistant Examiner—Raymond J. Henley, III
Attorney, Agent, or Firm—Young & Thompson

[57] ABSTRACT

The present invention relates to $\alpha,\beta$-dimethylhistamine, of the formula:

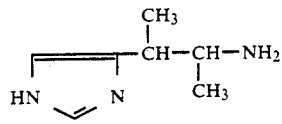

in racemic form, or an optical isomer form or mixture of diastereoisomers and its acid addition salts. It may be prepared from an alkyl 2-amino 3-(1H-imidazol-4-yl)-carboxylate.

5 Claims, No Drawings

HISTAMINE DERIVATIVE, PROCESS FOR PREPARING IT AND ITS THERAPEUTIC USE

This application is a CIP of application Ser. No. 217,222, now abandoned, which is a CIP of No. 901,750 (Pat. No. 4,767,778) disclosing a pharmaceutical composition containing as the active ingredient a compound according to the formula

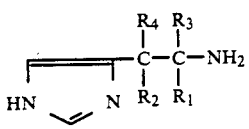

in which each of $R_1$, $R_2$ and $R_4$ represents a hydrogen or a methyl, or $R_1$ and $R_2$ taken together represent a methylene, and $R_3$ is a hydrogen, a methyl or a carboxy, with the proviso that $R_1$, $R_2$, $R_3$ and $R_4$ are not simultaneously hydrogen, and a pharmaceutically acceptable carrier or diluent.

The present invention relates to a new histamine derivative, a process for preparing it and to pharmaceutic compositions containing it.

The above patent is concerned more particularly with compounds known as such, but whose agonist properties on the $H_3$ receptors inducing release and synthesis of histamine were discovered.

It has now be found that α,β-dimethylhistamine, which compound is comprised in formula I above but has never been disclosed, has an agonist activity on the $H_3$ receptors which is more selective and generally higher than for the other compounds of this structure.

The present invention relates to α,β-dimethylhistamine, of the formula:

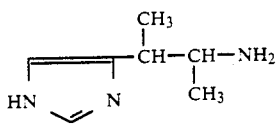

in racemic form, or an optical isomer form or a mixture of diastereoisomers, and its addition salts with pharmaceutically acceptable acids.

This compound having two asymmetric carbon atoms in its side chain exists in the form of 4 optical isomers.

A process for preparing the compound of the invention is characterized in that a ($C_1$–$C_6$)alkyl 2-amino 3-(1H-imidazol-4-yl)-butyrate is reduced by means of a metal hydride into 2-amino 3(1H-imidazol-4-yl)-butanol, said butanol derivative is transformed into 2-amino 1-chloro 3-(1H-imadazol-4-yl)-butane by means of a chlorinating agent, and said chloro derivative is catalytically reduced.

The alkyl (e.g. methyl) 2-amino 3-(1H-imidazol-4-yl)-butyrate starting product in his process may be prepared for example from (1-triphenylmethyl-1H-imidazol-4-yl)carbaldehyde according to J. L. Kelley, C. A. Miller and Ed. W. Mc Lean, J. Med. Chem 20, 721 (1977), and the latter compound is available from (1H-imidazol-4-yl)methanol according to P. Dziuron and W. Schunack, Arch. Parm. (Weinheim, W. Germany) 306, 347 (1973), and M. Barnabe and A. Burger, J. Med. Chem. 14, 883 (1971).

The invention provides also a sterospecific process for preparing the compound of the invention, characterized in that a ($C_1$–$C_6$)alkyl (1H-imidazol-4-yl)-carboxylate, the imidazole moiety of which has been protected (e.g. by a triphenylmethyl group), is transformed into erythro -α, β-dimehtylhistamine and the (+) and (−) enantiomers of this erythro compound are separated by means of an optically active acide.

The following Example shows the synthesis of the compound of the invention in the racemic form, namely from step i).

EXAMPLE 1

Preparation of [3-(1H-Imidazol-4-yl)but2-yl]amine or α,β-dimethylhistamine

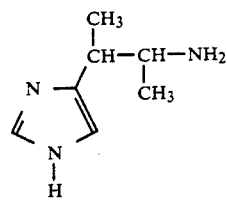

a) (1H-Imidazol-4-yl)methanol 52.06 g (0.5 mol) formamidine acetate and 45.04 g (0.5 mol) 1.3-dihydroxypropan-2-one are added in portions to 250 ml of liquid ammonia. The mixture is filled into a steelbomb and allowed to react for 12 hours at 40° C., 10 bar. Subsequently the mixture is delivered from the ammonia by evaporation. The resulting yellow sirup is dissolved in 500 ml 2-propanol and brought to pH 2 by dry HCl-gas. The voluminous precipitation is filtered off and extracted with 500 ml hot 2-propanol in 3 portions. An addition of 200 ml diethyl ether to the combined filtrates and storing at −25° C. results 57.1 g (84.9%) (1H-imidazol-4-yl)methanol hydrochloride, light brown crystals, melting point: 102° C.

$C_4H_6N_2O.HCl$ (134.6)

MS: m/z (rel. int. [%])=98 (M+, 47), 97 (53), 70 (15), 69 (44), 17 (100).

$^1$H-NMR data: ([$D_6$]DMSO, TMS as internal standard) δ=4.51 (s) 2H, 7.47 (d) 1H, 9.02 (d) 1H, ppm.

b) (1-Triphenylmethyl-1H-imidazol-4-yl)methanol

To a stirred solution of 18.8 g (140 mmol) (1H-imidazol-4-yl)methanol in 140 ml dimethylformamide and 50 ml triethylamine 40.5 g (145 mmol) triphenylmethylchloride in 300 ml dimethylformamide are dropped. After stirring for 2 hours at ambient temperature the reaction mixture is poured upon 2 kg of crushed ice. The precipitate is washed with water and impurities are removed by digestion with 400 ml warm dioxane. Collection, washing with diethyl ether and drying in vacuo yields 41 g (86%) of (1-Triphenylmethyl-1H-imidazol-4-yl)-methanol as a white powder, melting point: 224°–227° C.

$C_{23}H_{20}N_2O$ (340.4)

MS: m/z (rel. int. [%])=340 (M+., <1), 243 (100), 165 (64).

$^1$H-NMR data: ([$D_6$]DMSO, TMS as internal standard) δ=3.14 (br) 1H, replaceable by $D_2O$, 4.56 (s) 2H, 6.77 (d) 1H, 7.20–7.40 (m) 15H, 7.55 (d) 1H, ppm.

c) (1-Triphenylmethyl-1H-imidazol-4-yl)carbaldehyde 68.1 g (0.2 mol) (1-triphenylmethyl-1H-imidazol-4-yl)-methanol and 177.9 g (2 mol) manganese dioxide are refluxed for 3 hours in 1.3 l dioxane. The hot suspension is filtered over 100 ml Celite in a Buchner funnel and washed with 0.5 l hot dioxane in three portions. The solution is evaporated in vacuo and the white solid residue dried in vacuo. Yield: 49.1 g (72.5%), melting point: 188°–193° C.

C₂₃H₁₈N₂O (338.4)

MS: m/z (rel. int. [%]) = 338 (M⁺, <1), 243 (100), 165 (56).

¹H-NMR data: ([D₆]DMSO, TMS as internal standard) δ = 7.01–7.43 (m) 15H, 7.53 (d) 1H, 7.61 (d) 1H, 9.87 (s) 1H, ppm.

d) 1-(1-Triphenylmethyl-1H-imidazol-4-yl)ethanol

To a freshly prepared solution of 290 mmol methyl magnesium iodide in 700 ml diethyl ether 49.1 g (145 mmol) (1-triphenylmethyl-1H-imidazol-4-yl)-carbaldehyde in 200 ml tetrahydrofurane is dropped. The mixture is allowed to react 2 hours at ambient temperature, subsequently a solution of 19.4 g (0.36 mol) ammonium chloride in 70 ml water is added. After stirring overnight the precipitate is removed by filtration and washed with 300 ml tetrahydrofurane. The combined filtrates are diluted with 300 ml diethyl ether and washed with water. The organic phase is dried over sodium sulphate. Evaporation yields 46.5 g (90.4%) of 1-(1-triphenylmethyl-1H-imidazol-4-yl)-ethanol as a white powder, melting point: 156°–157° C.

C₂₄H₂₂N₂O (354.5)

MS: m/z (rel. int. [%]) = 354 (M⁺, <1), 243 (100), 165 (50).

e) 1-Chloro-1-(1H-imidazol-4-yl)ethane 46.1 g (130 mmol) 1-(1-triphenylmethyl-1H-imidazol-4-yl)ethanol are solved in 500 ml 2N hydrochloric acid and heated at 70° C. for 1 hour. The precipitate is removed by filtration. The solution is washed with 300 ml diethyl ether in 2 portions and evaporated in vacuo to afford 1-(1H-imidazol-4-yl)ethanol hydrochloride³⁾ as a faintly yellow oil. 100 ml thionyl chloride are dropped to the oil at 0° C., and the solution is allowed to react at ambient temperature overnight. Evaporation and crystallization with diethyl ether/ethylene glycole dimethyl ether affords 19.1 g (88%) of 1-chloro-1-(1H-imidazol-4-yl)ethane hydrochloride. Yellow crystals, melting point: 101°–104° C.

C₅H₇ClN₂.HCl (167)

MS: m/z (rel. int. [%] = 130 (M⁺, 1), 95 (72), 94 (74), 38 (100).

¹H-NMR data: ([D₆]DMSO, TMS as internal standard) δ = 1.88 (d) 3H, 5.51 (q) 1H, 7.77(d) 1H, 9.19 (d) 1H, ppm.

f) Diethyl 2-acetamido-2-[1-(1H-imadazol-4-yl)ethyl]propane-1.3-dicarboxylate 11.9 g (55 mmol) diethyl acetamidomalonate are added to a solution of 105 mmol sodium ethylate in 100 ml ethanol. After stirring for 2 hours the solution is cooled to 0° C. and 8.4 g (50 mmol) 1-chloro-1-(1H-imidazol-4-yl)ethane hydrochloride are added. The mixture is stirred for 2 hours, concentrated in vacuo and solved in 100 ml of 2% hydrochloric acid. This solution is extracted with 50 ml diethyl ether, brought to pH 8 by addition of sodium carbonate and extracted with 200 ml methylene chloride in 4 portions. The methylene chloride layers are combined, dried over sodium sulphate and evaporated in vacuo, affording 13.8 g (88.7%) diethyl 2-acetamido-2-[1-(1H-imidazol-4-yl)ethyl]propane-1.3-dicarboxylate as a light brown oil.

C₁₄H₂₁N₃O₅ (311.3)

MS: m/z (rel. int. [%]) = 311 (M⁺,48), 252 (60), 238 (43), 196 (54), 174 (42), 160 (56), 148 (61), 96 (79), 95 (90), 29 (100).

¹H-NMR data: ([D₆]DMSO, TMS as internal standard) d = 0.99–1.44 (m) 9H, 1.95 (s) 3H, 3.62–4.14 (m) 5H, 6.84–6.96 (m) 1H, 7.69 (d) 1H, 7.98 (br) 1H, replaceable by D₂O, ppm.

g) 2-Amino-3-(1H-imidazol-4-yl)butyric acid 13.1 g (42 mmol) diethyl 2-acetamido-2-[1-(1H-imidazol-4-yl)ethyl]propane-1.3-dicarboxylate are heated under reflux for 12 hours in 100 ml concentrated hydrochloric acid. After cooling and evaporation in vacuo 9.8 g (96%) of 2-amino-3-(1H-imidazol-4-yl)butyric acid dihydrochloride are obtained as a foam.

C₇H₁₁N₃O₂.2HCl (242.1)

¹H-NMR data: ([D₆]DMSO, TMS as internal standard) δ = 1.32–1.42 (m) 3H, 3.61–3.69. (m) 1H, 4.36–4.46 (m) 1H, 7.54 (d) 1H, 8.5–9.1 (br) 3H, replaceable by D₂O, 9.16 (d) 1H, 14.75 (br) 2H, replaceable by D₂O, ppm.

h) Methyl 2-amino-3-(1H-imidazol-4-yl)butyrate 9.40 g (38.9 mmol) of 2-amino-3-(1H-imidazol-4-yl)butyric acid dihydrochloride are solved in 100 ml methanol. Dry HCl-gas is bubbled through the solution while heating under reflux for 4 hours. After cooling the excess hydrochloric acid is removed by evaporation in vacuo. Yield: 9.8 g (98%) methyl 2-amino-3-(1H-imidazol-4-yl)butyrate hydrochloride as an amorphous solid.

C₈H₁₃N₃O₂.2HCl (256.1)

MS: m/z (rel. int. [%]) = 183 (M⁺, <1), 124 (20), 109 (6), (94), 95 (100).

¹H-NMR data (base): ([D₆]DMSO, TMS as internal standard) δ = 1.09–1.27 (m) 3H, 2.89–3.72 (m) 5H, 5.84 (br) 2H, replaceable by D₂O, 6.76 (d) 1H, 7.49 (d) 1H, ppm.

i) 2-Amino-3-(1H-imidazol-4-yl)butanol 7.7 g (30 mmol) methyl 2-amino-3-(1H-imidazol-4-yl)butyrate hydrochloride are added at 0° C. to a stirred suspension of 3.4 g (90 mmol) lithium aluminium hydride in 125 ml tetrahydrofurane. Subsequently, the mixture is refluxed for 3 hours, cooled to 0° C. and and hydrolysed by addition of 6.5 ml water in 15 ml tetrahydrofurane. Stirring with 20 ml 5N sodium hydroxide solution affords a coarse-grained precipitate which is filtered off and extracted by means of 100 ml ethanol in 3 portions. Concentration of the fractions affords an oil which is treated with anhydrous ethanol to separate inorganic material. Filtration and evaporation yield 4 g (85.9%) 2-amino-3-(1H-imidazol-4-yl)butanol wich is converted into the oily dihydrochloride. An analytical sample is converted into dipicrate and recrystallized from ethanol/water. Yellow crystals, melting point 168° C.

C₇H₁₃N₃O.2 C₆H₃N₃O₇ (613.4) Molar mass 155 (FAB-MS) Calc.: C 37.20, H 3.12, N 20.55, Found: C 37.23, H, 3.08, N 20.40.

¹H-NMR data: ([D₆]DMSO, TMS as internal standard) δ = 1.32 (m) 3H, 3.26–3.79 (m) 5H, 1H replaceable by D₂O, 7.49–7.56 (m) 1H, 7.87 (br) 3H, replaceable by D₂O, 8.63 (s) 4H, 9.12 (d) 1H, ppm.

j) 2-Amino-1-chloro-3-(1H-imidazol-4-yl)butane 3 g (13.2 mmol) 2-amino-3-(1H-imidazol-4-yl)butanol dihydrochloride are solved in a mixture of 25 ml tetramethylenesulfone and 10 ml thionyl chloride and stirred 12 hours at room temperature. Dropwise addition of 200 ml chloroform affords 2-amino-1-chloro-3-(1H-imidazol-4-yl)butane dihydrochloride. Yield: 2.87 g (88.2%) of a hygroscopic precipitate.

C₇H₁₂ClN₃.2HCl (246.6)

MS: m/z (rel. int. [%]) = 173 (M$^{30}$, <1), 137 (7), 96 (98), 95 (100).

$^1$H-NMR data: ([D$_6$]DMSO, TMS as internal standard) δ = 1.37 (d) 3H, 3.42-3.55 (m) 1H, 3.77-3.86 (m) 1H, 4.03 (d) 2H, 7.49-7.56 (m) 1H, 8.75 (br) 3H, replaceable by D$_2$O, 9.15 (d) 1H, 14.7 (br) 2H, replaceable by D$_2$O, ppm.

An analytical sample is converted into the dipicrate, yellow crystals, melting point 196°-198° C. from ethanol/water.

C$_7$H$_{12}$ClN$_3$.2 C$_6$H$_3$N$_3$O$_7$ (631.9) Calc.: C 36.12; H 2.87; N 19.95; Found: C 36.25; H 2.76; N 19.86.

k) [3-(1H-Imidazol-4-yl)but-2-yl]amine (R.S:R.S)

A mixture of 2 g (8.1 mmol) 2-amino-1-chloro-3-(1H-imidazol-4-yl)butane dihydrochloride, 1.3 g (16.2 mmol) sodium acetate and 100 ml 10% acetic acid, are hydrogenated over 0.5 g 10% palladium on activated carbon for 10 days at 10 bar and ambient temperature. The catalyst is removed by filtration and the filtrate brought to pH 1 by addition of concentrated hydrochloric acid. After evaporation the oily residue is dissolved in dry ethanol and inorganic material is removed by filtration. By addition of petrolether the title compound crystallizes as dihydrochloride. Recrystallization from methanol/acetonitrile yields 0.72 g (40.4%) [3-(1H-imidazol-4yl)but-2-yl]amine.2HCl.0.25 methanol as colorless crystals, melting point: 249°-254° C. (decomp.).

C$_7$H$_{13}$N$_3$.2 HCl.0.25 CH$_4$O (220.1) Calc.: C 39.56; H 7.33; N 19.09; Found: C 39.50; H 7.40; N 19.15.

MS: m/z (rel. int. [%]) = 140 (11), 139 (M$^+$, 1), 124 (14), 96 (95), 81 (35), 44 (100).

$^1$H-NMR data: ([D$_6$]DMSO, TMS as internal standard) δ = 1.10-1.36 (m) 6H, 3.28 (m) 1H, 3.40 (m) 1H, 7.51-7.58 (m) 1H, 8.36 (br) 3H, replaceable by D$_2$O, 9.12 (d) 1H, 14.76 (br) 2H, replaceable by D$_2$O, ppm

EXAMPLE 2

Preparation of (−)- and (+)-erythro-[3-(1H-Imidazol-4-yl)but-2-yl]amine l) Methyl (1H-imidazol-4-yl) carboxylate 112.09 g (1 mol) (1H-imidazol-4-yl)carboxylic acid are added to 1.3 l methanol. Dry HCl-gas is bubbled through the mixture which is heated under reflux for 4 hours. Cooling to room temperature and evaporation to 300 ml afford 98 g of the title compound as white crystals. Repeated evaporation leads to 46.5 g additional material (total: 144.5 g, 88.9%). An analytical sample is recrystallized from methanol, melting point: 173°-174° C. (ref.[1]) mp: 156° C.).

C$_5$H$_6$N$_2$O$_2$.HCl (162.6) Calc.: C 36.94; H 4.34; N 17.23; Found: C 36.93; H 4.44; N 17.23.

MS: m/z (rel.int. [%]) = 126 (M$^+$, 63), 95 (100), 67 (41), 40 (68).

$^1$H-NMR data: ([D6]DMSO, TMS as internal standard) δ = 12.97 (br) 2H, replaceable by D$_2$O, 9.29 (d) 1H, 8.37 (d) 1H, 3.90 (s) 3H, ppm.

m) Methyl (1-triphenylmethyl-1H-imidazol-4-yl)carboxylate

To a solution of 151.79 g (1.5 mol) triethylamine in 1 l methylene chloride 97.55 g (0.6 mol) methyl (1H-imidazol-4-yl)carboxylate are added. After stirring for 1 hour at ambient temperature a solution of 183.99 g (0.66 mol) triphenylmethylchloride in 500 ml methylene chloride is dropped to the mixture, which subsequently is allowed to react for 1 hour. When the reaction is completed the mixture is washed 4 times with 200 ml water, dried by means of sodium sulphate and evaporated to dryness. The resulting oil crystallizes on standing overnight. Pulverizing and washing 3 times with 200 ml warm diethyl ether lead to 210.2 g (95.1%) methyl (1-triphenylmethyl-1H-imidazol-4-yl)carboxylate as light yellow crystals. An analytical sample was recrystallized from methanol resulting white crystals, melting point: 147°-152° C. (ref.[2]) 145°-146° C.).

C$_{24}$H$_{20}$N$_2$O$_2$ (368.5) Calc.: C 78.24; H 5.47; N 7.60; Found: C 77.96; H 5.23; N 7.66.

MS: m/z (rel. int. [%]) = 368 (M$^+$, 30), 258 (100).

$^1$H-NMR data: (CDCl$_3$, TMS as internal standard) δ = 7.58 (d) 1H 7.47-7.01 (m) 16H, 3.85 (s) 3H, ppm.

n) Ethyl 3-oxo-3-(1-triphenylmethyl-1H-imidazol-4-yl)propionate 202.65 g (0.55 mol) methyl (1-triphenylmethyl-1H-imidazol-4-yl)carboxylate are dissolved in 0.8 l dry toluene at 85° C. 44 g (1.1 mol) sodium hydride (60% dispersion in mineral oil) are added. To the stirred mixture 96.92 g (1.1 mol) ethyl acetate are dropped over 2 hours. The mixture is allowed to react 16 hours at 70° C. Subsequently the toluene is removed under reduced pressure. The resulting mixture is introduced into the following step without purification. For analytical purposes a small amount of the brown oily residue is dissolved in methylene chloride, washing with aqueous ammonium chloride solution and water, drying by means of sodium sulphate and evaporation lead to an oil. Crystallization with diethyl ether and recrystallization from ethanol/diethyl ether afford the title compound as white crystals, melting point 136°-139° C.

C$_{27}$H$_{24}$N$_2$O$_3$ (424.5) Calc.: C 76.39; H 5.70; N 6.60; Found: C 76.30; H 5.66; N 6.47.

MS: m/z (rel. int. [%]) = 424 (M$^+$, <1), 244 (19), 243 (100).

$^1$H-NMR data: (CDCl$_3$, TMS as internal standard) δ = 7.62 (d) 1H, 7.55-6.99 (m) 16H, 4.61 (q) 2H, 3.99 (s) 2H, 1.24 (t) 3H, ppm.

o) 1-(1-Triphenylmethyl-1H-imidazol-4-yl)ethanone

The residue from n) is dissolved in a mixture of 75 g potassium hydroxide, 140 ml water and 1.3 l ethanol. The solution is heated under reflux for 10 hours. Solid material is removed by filtration. After evaporation and dissolving in methylene chloride it is washed 3 times with 400 ml water (addition of 2-propanol separates the layers), dried by sodium sulphate and evaporated. Stirring and addition of diethyl ether afford 115.3 g 1-(1-triphenylmethyl-1H-imidazol-4-yl)ethanone (59.5% based on m)) as light yellow crystals. An analytical probe is recrystallized from ethanol: white crystals, melting point 164°-165° C.

C$_{24}$H$_{20}$N$_2$O (352.4) Calc.: C 81.79; H 5.72; N 7.95; Found: C 81.67; H 5.64; N 8.03.

MS: m/z (rel.int. [%]) = 352 (M$^+$, <), 244 (22), 243 (100), 183 (85).

$^1$H-NMR data: (CDCl$_3$, TMS as internal standard) δ = 7.45-7.20 (m) 17H, 3.06 (s) 3H, ppm.

p) (Z)-Ethyl 2-methyl-3-(1-triphenylmethyl-1H-imidazol-4-yl)2-butenate 11.7 g (0.3 mol) sodium amide are suspended in 300 ml tetrahydrofurane under nitrogene. 71.47 g (0.3 mol) triethyl 2-phosphonopropionate are dropped to the stirred mixture which is kept at ambient temperature for 2 hours subsequently. 30.5 g (86.5 mmol) 1-(1-triphenylmethyl-1H-imidazol-4-yl)ethanone are added and the mixture is held under reflux for 16 hours. Evaporation and dissolving in 1 l chloroform/2-propanol (3:1) is follwed by washing 3 times with water. Drying with sodium sulphate and evaporation result an oil which mainly consists of E-ethyl 2-methyl-3-(1-triphenylmethyl-1H-imidazol-4-yl)2-butenate. Treating this residue with diethyl ether affords 10.9 g of a solid material mainly consisting of the Z-isomer. Purification via column chromatography (silicagel 63–200 μm, eluent: petrol ether/diethyl ether [2:2]) leads to 5.6 g (14.8%) of the title compound as a white solid. An analytical sample was recrystallized from diethyl ether/ethanol resulting colourless crystals, melting point 166°–168° C.

$C_{29}H_{28}N_2O_2$ (436.6) Calc.: C 79.79; H 6.46; N 6.43; Found: C 79.49; H 6.43; N 6.34.

MS: m/z (rel. int. [%]) = 436 (M+, 2), 244 (20), 243 (100), 165 (23).

$^1$H-NMR data: (CDCl$_3$, TMS as internal standard) δ = 7.58–7.11 (m) 16H, 6.76 (d) 1H, 4.07 (q) 2H, 1.98 (s) 6H, 1.17 (t) 3H, ppm.

q) erythro-Ethyl 3-(1H-imidazol-4-yl)2-methylbutanate 10.2 g (23.4 mmol) Z-ethyl 2-methyl-3-(1-triphenylmethyl-1H-imidazol-4-yl)2-butenate are dissolved in 350 ml tetrahydrofurane, 1.5 g 10% palladium on activated carbon are added. The mixture is hydrogenated for 3 days at ambient temperature and 10 bar. After removal of the catalyst by filtration the solution is evaporated to dryness. The residue is purified by column chromatography (silicagel 63–200 μm, eluent 1: diethyl ether, eluent 2: chloroform/methanol saturated with ammonia [1:1]) leading to 3.9 g (84.9%) erythro-ethyl 3-(1H-imidazol-4-yl)2-methylbutanate as a colourless oil. A small amount is converted into the hydrogenmaleate resulting white crystals, melting point 91°–94° C. (ethanol/diethyl ether).

$C_{10}H_{16}N_2O_2.C_4H_4O_4$ (312.3) Calc.: C 53.84; H 6.45; N 8.97; Found: C 53.72; H 6.60; N 8.82.

MS: m/z (rel. int. [%]) = 196 (M+, 11), 123 (30), 95 (100); obtained from a sample of q.HCl.

$^1$H-NMR data: ([D6]DMSO, TMS as internal standard) δ = 8.88 (s) 1H, 7.46 (s) 1H, 6.05 (s) 2H, 4.08 (q) 2H, 3.10 (dq) 1H, 2.70 (dq) 1H, 1.22–1.13 (m) 6H, 0.95 (d) 3H, ppm.

(r) erythro-3-(1H-Imidazol-4-yl)2-methylbutanoic acid 3.8 g (19.4 mmol) erythro-ethyl 3-(1H-imidazol-4-yl)2-methylbutanate are dissolved in 60 ml 6M hydrochloric acid and heated under reflux for 5 hours. Evaporation affords erythro-3-(1H-imidazol-4-yl)2-methylbutanoic acid hydrochloride as a hygroscopic oil which is introduced into the next step without purification.

$C_8H_{12}N_2O_2.HCl$ (204.7)

MS: m/z (rel.int. [%]) = 168 (M+, 17), 123 (19), 95 (100), 68 (10).

$^1$H-NMR data: ([D6]DMSO, TMS as internal standard) δ = 9.04 (s) 1H, 7.51 (s) 1H, 3.10 (m) 1H, 2.63 (m) 1H, 1.24 (d) 3H, 0.93 (d) 3H, ppm.

(s) erythro-[3-(1H-Imidazol-4-yl)but-2-yl]amine

To a solution of erythro-3-(1H-imidazol-4-yl)2-methylbutanoic acid hydrochloride in 20 ml concentrated sulphuric acid 125 ml chloroform are added. The mixture is stirred and 5.85 g (90 mmol) sodium azide are added over 1 hour at 0° C. Subsequently the reaction mixture is held at 45° C. for 14 hours. After addition of some ice the organic layer is removed. The aqueous phase is brought to pH 8.5 and evaporated to dryness. Soxhletizing of the resulting solid material for 3 hours by means of 2-butanol affords the title compound as a crude oil which is purified via column chromatography (silicagel 63–200 μm, eluent: chloroform/methanol saturated with ammonia [85:15]) affording 2.32 g (85.9% based on q) erythro-[3-(1H-imidazol-4-yl)but-2-yl]amine as a colourless oil. An analytical sample is converted into the dipikrate: yellow crystals, melting point: 228–232° C. (ethanol).

$C_7H_{13}N_3.2\ C_6H_3N_3O_7$ (597.4) Calc.: C 38.20; H 3.21; N 21.10; Found: C 38.22; H 3.15; N 21.14.

$^1$H-NMR data: ([D6]DMSO, TMS as internal standard) δ = 9.09 (s) 1H, 8.60 (s) 4H, 7.81 (br) 3H, replaceable by D$_2$O, 7.55 (s) 1H, 3.40 (m) 1H, 3.15 (m) 1H, 1.30 (d) 3H, 1.09 (d) 3H, ppm.

t) (−)-erythro-[3-(1H-Imidazol-4-yl)but-2-yl]amine di[(+)-2S,3S-di-O-(4-toluoyl)hydrogentartrate] monohydrate 0.56 g (4 mmol) erythro-[3-(1H-imidazol-4-yl)but-2-yl]amine are dissolved in 30 ml hot ethanol/water (1:1) and added to a hot solution of 3.13 g (8.1 mmol) (+)-2S,3S-di-O-(4-toluoyl)tartaric acid in 80 ml hot ethanol/water (1:1). After standing for 3 days at room temperature the resulting white crystals are recrystallized from ethanol/water (1:1) until melting point and optical rotation are constant: 0.79 g (42.5%) of the title compound as white crystals, melting point 181° C.

$C_7H_{13}N_3.2\ C_{20}H_{18}O_8.H_2O$ (929.9) Calc.: C 60.71; H 5.53; N 4.52; Found: C 60.39; H 5.41; N 4.76.

$[\alpha]_D^{20} = +110.6(2)°$ (c = 0.1, MeOH)

u) (−)-erythro-[3-(1H-Imidazol-4-yl)but-2-yl]amine 0.77 g (−)-erythro-[3-(1H-imidazol-4-yl)but-2-yl]amine di[(+)-2S,3S-di-O-(4-toluoy)hydrogentartrate] monohydrate (0.83 mmol) are dissolved in 60 ml ethanol/water (2:1) and 0.5 ml of hydrobromic acid (47%) are added. Evaporation and redissolving in 20 ml water and 20 ml methylene chloride are followed by 4 times extraction with 20 ml methylene chloride. The aqueous solution is evaporated and delivered from excess hydrobromic acid by multiple dissolving in ethanol and evaporation. Adding diethyl ether and 2-propanol followed by stirring afford 0.18 g (72%) (−)-erythro-[3-(1H-imidazol-4-yl)but-2-yl]amine dihydrobromide as white crystals, melting range: 207°–230° C.

$C_7H_{13}N_3.2\ HBr$ (301.0) Calc.: C 27.93; H 5.02; N 13.96; Found: C 27.80; H 5.05; N 13.65.

$^1$H-NMR data: ([D6]DMSO, TMS as internal standard) δ = 14.22 (br) 2H, replaceable by D$_2$O, 9.14 (s) 1H, 7.98 (br) 3H, replaceable by D$_2$O, 7.59 (s) 1H, 3.37 (m) 1H, 3.23 (m) 1H, 1.32 (d) 3H, 1.12 (d) 3H, ppm.

$[\alpha]_D^{20} = -6.2(1)°$ (c = 0.5, H$_2$O)

v) (+)-erythro-[3-(1H-Imidazol-4-yl)but-2yl]amine di[(−)-2R,3R-di-O-(4-toluoyl)hydrogentartrate] monohydrate The filtrate of the first crystallisation under t) is evaporated to dryness and converted into the dihydrobromide (analogously to t). Dissolving in dry ethanol and addition of an equivalent amount potassium tert. butylate result after filtration and evaporation 0.17 g (1.2 mmol) erythro-[3-(1H-Imidazol-4-yl)but-2-yl] amins as free base. The base is dissolved in 10 ml hot ethanol/water (1:1) and given to a solution of 1.07 g (2.5 mmol) (−)-2R,3R-di-O-(4-toluoyl)tartaric acid in 30 ml hot ethanol/water (1:1). After standing for 3 days at ambient temperature the resulting white crystals are recrystallized from ethanol/water (1:1) until melting point and optical rotation are constant, resulting 0.21 g (11.3% based on the educt in t)) white crystals, melting point 181° C.

$C_7H_{13}N_3.2\ C_{20}H_{18}O_8.H_2O$ (929.9) Calc.: C 60.71; H 5.53; N 4.52; Found: C 60.52; H 5.34; N 4.69.

$[\alpha]_D^{20} = -109.4(2)°$ (c = 0.1, MeOH)

w) (+)-erythro-[3-(1H-Imidazol-4-yl)but-2-yl]amine 0.2 g (0.22 mmol) (+)-erythro-[3-(1H-imidazol-4-yl)but-2-yl]amine di[(−)-2R,3R-di-O-(4-toluoyl)hydrogentartrate] monohydrate are converted into the dihydrobromide in the way described in μ) resulting 60 mg (86.7%) (+)-erythro-[3-(1H-Imidazol-4-yl)but-2-yl]amine as white crystals, melting range 209°–230° C. (diethyl ether/2-propanol).

$C_7H_{13}N_3 \cdot 2$ HBr (301.0) Calc.: C 27.93; H 5.02; N 13.96; Found: C 27.65; H 5.07; N 13.60.

$[\alpha]D20 = +5.7(1.5)°$ (c=0.5, $H_2O$)

Pharmacological investigation.

The compound of the invention was investigated in racemic and stereoisomeric form.

a) The inhibition of the release of histamine induced by depoliarization of slices of rat brain was studied according to the method described by Arrang and al. (Nature, 1983, 302, 832–837). The maximal inhibition induced by the compound of the invention is identical to that induced by histamine (it is a complete agonist) and its 50% inhibitory concentration (IC50) is the following:

racemic form: $12 \times 10^{-9}$M
erytro form: $6 \times 10^{-9}$M
(+)erythro isomer: $3.4 \pm 2, 0 \times 10^9$M
(−)erythro isomer: $48 \pm 31 \times 10^{-9}$M
threo form: $200 \times 10^{-9}$M It may be seen that the activity of the compound of the invention on the $H_3$ receptors is selectively provided by one of the four stereoisomers, i.e. the (+) erythro enantiomer. The activity of the (−) erythro enantiomer is probably lower than above, as this compound was about 85% pure and contained some (+) erythro enantiomer.

b) Contraction of the isolated ileum of guinea pig: the compound is a complete agonist, but has less than 1/1000th of the activity of histamine.

c) Contraction of the isolated auricle of guinea a pig: the compound is a partial agonist (the maximal effect is 60% of that of histamine) and about 1000 times less active than histamine.

The results are summarized in the following table.

TABLE

Activity of he compound of the invention compared with that of histamine (activity = 100) on the three classes of histaminergic receptors.

| | $H_3^{(a)}$ | $H_1^{(b)}$ | $H_2^{(c)}$ |
|---|---|---|---|
| histamine | 100 | 100 | 100 |
| α,β-diethylhistamine | | | |
| racemic | 516 | 0.06 | 0.01 |
| erythro | 1030 | | |
| (+)erythro | 1800 | | |
| (−)erythro | 129 | | |

Further the compound was found active in vivo since at the dose of 20 mg/kg (racemic) by the oral route it inhibits the synthesis of histamine in the rat brain (mesured according to the test of Arrang et al., Nature 1987, 327, 117).

This investigation shows that the compound of the invention has a very high and particularly selective $H_3$ activity, whereas its activity on the $H_1$ and $H_2$ receptors is insignificant, about 10 to 100 times lower than that of the best compounds known form Kokai 62-123 174. Consequently it can be a powerful and selective $H_3$ agonist which may be used in therapy in better conditions of security.

In consequence, it is likely to decrease histaminergic transmission in the digestive tract and in the nervous, cardiovascular and immune systems. It can be used in therapy as a drug having sedative effects, as a sleep regulator, anticonvulsant, regulator of hypothalamo-hypophyseal secretion, antidepressant, modulator of cerebral circulation, and the like.

Furthermore, inhibition of the release of inflammation messengers in various allergic conditions (e.g. asthma) is expected to result from the stimulation of the $H_3$ receptors of the lung, for example.

In gastroenterology, the inhibition of release of gastric histamine is likely to exert antisecretory and antiulcerative effects. Modification of release of the messengers of immune responses is likely to modulate the latter responses.

By virtue of these novel and unexpected properties, the compound of the invention mainly in the form of its (+) erythroisomer, may be used for treating diseases which involve histamine synthesis and release in the human or animal body. Thus, the invention provides a method for treating a patient suffering from such a disease by administering a therapeutically effective amount of the compound of the invention. From its mode of action, its diverse pharmacological effects and its low toxicity in animals, apllications of this derivative may be predicted both in human and veterinary medicine, at doses of the order of 0.1 to 10 mg/kg administered, in particular, orally or parenterally.

It can be presented, in particular, in the form of tablets, dragees, gelatine capsules, aerosols, injectable solutions or suppositories.

We claim:

1. α, β-dimethylhistamine or a pharmaceutically acceptable acid salt thereof.

2. Erythro-α, β-dimethylhistamine or a pharmaceutically acceptable acid addition salt thereof.

3. (+) Erythro-α, β-dimethylhistamine or a pharmaceutically acceptable acid addition salt thereof.

4. A process for the preparation of α, β-dimethylhistamine comprising reducing an alkyl 2-amino-3-(1H-imidazol-4-yl)butyrate to 2-amino-3-(1H-imidazol-4-yl)butanol by means of a metal hybride, converting said butanol derivative into 2-amino-1-chloro-3-(1H-imidazol-4-yl)butane by means of a chlorinating agent, and catalytically reducing said butane derivative.

5. The process according to claim 4, wherein said chlorinating agent is thionyl chloride.

* * * * *